United States Patent
Souda et al.

(10) Patent No.: US 6,750,370 B2
(45) Date of Patent: Jun. 15, 2004

(54) PROCESS FOR RACEMIZING OPTICALLY ACTIVE VINYL-SUBSTITUTED CYCLOPROPANECARBOXYLIC ACID COMPOUND

(75) Inventors: Hiroshi Souda, Toyonaka (JP); Kazunori Iwakura, Ibaraki (JP); Fumisato Goto, Ibaraki (JP)

(73) Assignee: Sumitomo Chemical Company, Limited, Osaka (JP)

( * ) Notice: Subject to any disclaimer, the term of this patent is extended or adjusted under 35 U.S.C. 154(b) by 24 days.

(21) Appl. No.: 10/195,409

(22) Filed: Jul. 16, 2002

(65) Prior Publication Data

US 2003/0032839 A1 Feb. 13, 2003

(30) Foreign Application Priority Data

Jul. 18, 2001 (JP) ......................................... 2001-217723

(51) Int. Cl.[7] ........................... C07C 61/04; C07B 55/00
(52) U.S. Cl. ........................................ 562/506; 562/401
(58) Field of Search .................................. 562/506, 401

(56) References Cited

U.S. PATENT DOCUMENTS

| 3,657,086 A | 4/1972 | Matsui et al. |
| 4,182,906 A | 1/1980 | Suzukamo et al. |

FOREIGN PATENT DOCUMENTS

| EP | 0 165 070 A2 | 12/1985 |
| EP | 0 235 940 A1 | 9/1987 |
| EP | 0 261 824 A1 | 3/1988 |
| EP | 0 282 221 A2 | 9/1988 |
| EP | 0 289 324 A1 | 11/1988 |
| EP | 0 299 760 A1 | 1/1989 |
| EP | 0 155 765 A1 | 9/1989 |
| JP | 61-167647 A | 7/1986 |
| JP | 62-4245 A | 1/1987 |
| JP | 63183550 A | 7/1988 |
| JP | 63-270639 A | 11/1988 |
| JP | 01261349 A | 10/1989 |
| JP | 2-73036 A | 3/1990 |
| JP | 2-169541 A | 6/1990 |
| JP | 03090082 A | 4/1991 |

*Primary Examiner*—Paul J. Killos
(74) *Attorney, Agent, or Firm*—Birch, Stewart, Kolasch & Birch, LLP

(57) ABSTRACT

There is disclosed a process for the racemization of a vinyl-substituted cyclopropanecarboxylic acid or a derivative thereof, which is characterized by reacting an optically active vinyl-substituted cyclopropanecarboxylic acid compound of formula (1):

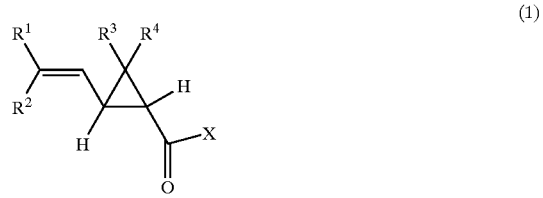

(1)

wherein $R^1$, $R^2$, $R^3$ and $R^4$ each independently represent
  a hydrogen atom, a halogen atom,
  alkyl which may be substituted having 1–4 carbon atoms,
  aryl which may be substituted, or
  alkoxycarbonyl which may be substituted, or
  $R^1$ and $R^2$ are bonded to form an alkylene group, which may be substituted; and wherein X represents hydroxyl, a halogen atom, alkoxy which may be substituted having 1–20 carbon atoms, or aryloxy which may be substituted,
with a nitric compound or a nitrogen oxide.

11 Claims, No Drawings

PROCESS FOR RACEMIZING OPTICALLY ACTIVE VINYL-SUBSTITUTED CYCLOPROPANECARBOXYLIC ACID COMPOUND

BACKGROUND OF THE INVENTION

Field of the Invention

The present invention relates to a process for racemizing an optically active vinyl-substituted cyclopropanecarboxylic acid compound.

Optically active vinyl-substituted cyclopropanecarboxylic acid compounds are known as important synthetic pyrethroid insecticides or production intermediates thereof, and a desired optical isomer thereof has been produced by optical resolution of a racemate thereof with an optical resolution agent. In connection with the optical resolution process, the other isomer of the resolved desired compound was racemized to the racemate for the purpose of efficiently utilizing the produced chemicals, and there have been reported, for example, a racemization method of an optically active chrysanthemum-monocarboxylic acid by reacting the optically active acid or its halide with a Lewis acid (e.g. aluminum bromide), and a method of irradiating light in the co-presence of thiol(SH), and the like (JP-A-52-144651, JP-A-60-174744, JP-A-61-5045, JP-A-1-261349).

However, these methods were not necessarily satisfactory as an industrial production process in that a halogen-containing catalyst, which is generally corrosive to reactors, was required, or a powerful electric energy supply for light-irradiation was required.

SUMMARY OF THE INVENTION

According to the present invention, an optically active vinyl-substituted cyclopropanecarboxylic acid compounds including carboxylic acids, carboxylic acid halides and carboxylic acid esters thereof, can be effectively racemized in an industrially advantageous manner.

The present invention provides a process for racemizing an optically active vinyl-substituted cyclopropanecarboxylic acid compound of formula (1):

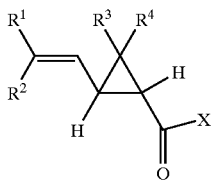

(1)

wherein $R^1$, $R^2$, $R^3$ and $R^4$ each independently represent
- a hydrogen atom, a halogen atom,
- an alkyl group having 1–4 carbon atoms, which may be substituted,
- an aryl group, which may be substituted, or
- an alkoxycarbonyl group, which may be substituted, or
- $R^1$ and $R^2$ are bonded to form an alkylene group, which may be substituted (e.g. haloalkylene group such as dihaloethylene group or the like); and X represents
- a hydroxyl group, a halogen atom, an alkoxy group having 1–20 carbon atoms, which may be substituted, or an aryloxy group, which may be substituted, which process comprises reacting said optically active vinyl-substituted cyclopropanecarboxylic acid compound of formula (1) with a nitric compound or a nitrogen oxide.

DETAILED DESCRIPTION OF THE INVENTION

"Racemizing" in the present process means that the optical rotatory power of said optically active vinyl-substituted cyclopropanecarboxylic acid compound of formula (1) to be reacted is decreased or lost.

A description will be first made to $R^1$, $R^2$, $R^3$ and $R^4$ of formula (1) above.

The alkyl group having 1–4 carbon atoms, which may be substituted, may be straight, branched, or cyclic, and the examples thereof include methyl, ethyl, n-propyl, i-propyl, cyclopropyl, n-butyl, sec-butyl, tert-butyl, and the like.

The alkyl group may be substituted with a group selected from:
- a halogen atom such as fluorine, chlorine, bromine, or iodine; and
- an alkoxy group (e.g. C1–C4 alkoxy) such as methoxy, ethoxy, n-propoxy, i-propoxy, n-butoxy, sec-butoxy, tert-butoxy, or the like.

Examples of the aryl group, which may be substituted include phenyl, and the aryl group may be substituted with an alkyl group (e.g. C1–C4 alkyl as described above), a halogen atom, or the like.

Examples of the alkoxycarbonyl group, which may be substituted include a (C1–C4)alkoxy-carbonyl group such as methoxycarbonyl, ethoxycarbonyl, n-propoxycarbonyl, i-propoxycarbonyl, n-butoxycarbonyl, sec-butoxycarbonyl, tert-butoxycarbonyl or the like.

Furthermore, these alkoxycarbonyl may be substituted with a halogen atom such as fluorine, chlorine, bromine, or iodine.

Preferably $R^1$ to $R^4$ represent a methyl group. Alternatively, $R^1$ and $R^2$ preferably represent a halogen atom and $R^3$ and $R^4$ represent a methyl group.

Examples of the alkoxy group, which may be substituted, represented by "X" in the formula (1), include an alkoxy group having 1–20 carbon atoms, which may be substituted, and an aryloxy group, which may be substituted.

The alkoxy group may be straight, branched or cyclic.

Specific examples of the alkoxy group include methoxy, ethyoxy, n-propoxy, isopropoxy, n-butoxy, sec-butoxy, tert-butoxy, n-pentoxy, neopentoxy, n-hexyloxy, cyclohexyl, n-heptyloxy, n-octyloxy, n-nonyloxy, n-decyloxy, n-undecyloxy, n-dodecyloxy, n-tridecyloxy, n-tetradecyloxy, n-pentadecyloxy, n-hexadecyloxy, n-heptadecyloxy, n-octadecyloxy, n-nonadecyloxy, n-icosyloxy and the like.

The alkoxy group may be substituted with a group selected from:
- a halogen atom such as fluorine, chlorine, bromine, and iodine;
- an aryl group, which may be substituted with an alkyl (e.g. C1–C3 alkyl such as methyl, ethyl, or propyl), or phenoxy group, and specific examples of the aryl group include, for example phenyl, naphthyl, or anthracenyl methylphenyl, dimethylphenyl, trimethylphenyl, propylphenyl, and phenoxyphenyl groups;
- a heterocyclic group such as furyl, phenoxyfuryl, benzylfuryl, difluoromethylfuryl, propargylfuryl, methylisoooxazolyl, trifluoromethylthiazolyl, trifluoromethoxythiazolyl, propinylpyrolyl, propinylpyrazolyl, propinyldioxoimidazolidinyl, indolyl, propinylindolyl, dioxotetrahydroisoindolyl, oxothiazolyl, pyridyl, or trifluoropyridyl group;

an oxo group;

an alkenyl having a double bond or an alkynyl having a triple bond (e.g. C2–C3 alkenyl such as vinyl, propenyl or the like, C2–C3 alkynyl such as ethynyl, propynyl or the like); cyano; nitro; and the like.

The alkoxy group, which may be substituted is preferably a C1–C20 alkoxy group, more preferably a C1–C4 alkoxy group, yet more preferably a C1–C2 alkoxy group.

Examples of the aryloxy group, which may be substituted, include phenoxy, 1-naphthyloxy, 2-naphthyloxy of which aromatic ring may be substituted with alkyl(e.g. C1–C4 alkyl), alkynyl(e.g. C2–C3 alkynyl), alkoxy(e.g. C1–C4 alkoxy), acetyl, formyl, or a halogen atom. Specific examples of the alkyl, alkynyl and alkoxy groups include those specified above.

Specific examples of the optically active vinyl-substituted cyclopropanecarboxylic acid compound of formula (1) include optically active 2,2-dimethyl-3-(1-propenyl)cyclopropanecarboxylic acid,
2,2-dimethyl-3-(2-methyl-1-propenyl)cyclopropanecarboxylic acid,
2,2-dimethyl-3-(2,2-dichlorovinyl)cyclopropane-carboxylic acid,
2,2-dimethyl-3-(2-chloro-2-fluorovinyl)cyclopropanecarboxylic acid,
2,2-dimethyl-3-(2-bromovinyl)cyclopropanecarboxylic acid,
2,2-dimethyl-3-(2,2-dibromovinyl)cyclopropanecarboxylic acid,
2,2-dimethyl-3-(2-chloro-3,3,3-trifluoro-1-propenyl)-cyclopropanecarboxylic acid,
2,2-dimethyl-3-{3,3,3-trifluoro-2-(trifluoromethyl)-1-propenyl}cyclopropanecarboxylic acid,
2,2-dimethyl-3-(2-phenyl-1-propenyl)cyclopropanecarboxylic acid,
2,2-dimethyl-3-(2-phenylvinyl)cyclopropanecarboxylic acid,
2,2-dimethyl-3-{(2,2-difluorocyclopropylidene)methyl}-cyclopropanecarboxylic acid,
2,2-dimethyl-3-{2-(tert-butoxycarbonyl)vinyl}-cyclopropanecarboxylic acid,
2,2-dimethyl-3-{2-fluoro-2-(methoxycarbonyl)vinyl}-cyclopropanecarboxylic acid,
2,2-dimethyl-3-{2-fluoro-2-(ethoxycarbonyl)vinyl}-cyclopropanecarboxylic acid,
2,2-dimethyl-3-{2-fluoro-2-(tert-butoxycarbonyl)-vinyl}cyclopropanecarboxylic acid,
2,2-dimethyl-3-[2-{2,2,2-trifluoro-1-(trifluoromethyl)-ethoxycarbonyl}vinyl]cyclopropanecarboxylic acid,
2-methyl-2-ethyl-3-(1-propenyl)cyclopropanecarboxylic acid,
2,2-diethyl-3-(2,2-dichlorovinyl)cyclopropanecarboxylic acid, and
2-methyl-2-phenyl-3-(2-methyl-1-propenyl)cyclopropanecarboxylic acid; optically active chlorides, methyl esters and ethyl esters thereof; and the like.

Preferable examples thereof include, for example, optically active 2,2-dimethyl-3-(1-propenyl)cyclopropanecarboxylic acid,
2,2-dimethyl-3-(2-methyl-1-propenyl)cyclopropanecarboxylic acid,
2,2-dimethyl-3-(1-propenyl)cyclopropanecarboxylic acid chloride,
2,2-dimethyl-3-(2-methyl-1-propenyl)cyclopropanecarboxylic acid chloride,
ethyl 2,2-dimethyl-3-(1-propenyl)cyclopropanecarboxylate,
ethyl 2,2-dimethyl-3-(2-methyl-1-propenyl)cyclopropanecarboxylate, and the like.

Said optically active vinyl-substituted cyclopropanecarboxylic acid compound of formula (1) means, for example, a (+)-vinyl-substituted cyclopropanecarboxylic acid compound, a (−)-vinyl-substituted cyclopropanecarboxylic acid compound, or a mixture thereof containing one of them in excess (enriched with one isomer).

The (+)-vinyl-substituted cyclopropanecarboxylic acid compound and a (−)-vinyl-substituted cyclopropanecarboxylic acid compound have a trans isomer or a cis isomer based on the relative configurations at the cyclopropane carbon atoms connected with the carbonyl carbon atom and the vinyl group respectively. Thus, said optically active vinyl-substituted cyclopropanecarboxylic acid compound of formula (1) means (+)-trans, (+)-cis, (−)-trans, or (−)-cis isomer, or a mixture thereof enriched with (+)-isomer(s) or (−)-isomer(s).

Examples of the nitric compound, which may be used in the present invention include, for example, nitric acid, nitrate (a salt or ester of nitric acid) and a mixture of nitric acid and nitrate. The concentration of the nitric acid is not particularly limited. The salt of nitric acid includes a metal salt of nitric acid or a double salt of nitric acid.

Specific examples of the salt of nitric acid include zinc (II) nitrate, aluminum nitrate, ammonium nitrate, diammonium cerium (III) nitrate, diammonium cerium (IV) nitrate, ytterbium (III) nitrate, yttrium nitrate, indium (III) nitrate, erbium nitrate, cadmium nitrate, gadolinium nitrate, gallium nitrate, calcium nitrate, silver nitrate, chromium (II) nitrate, chromium (III) nitrate, cobalt (II) nitrate, samarium nitrate, zirconium nitrate, zirconyl nitrate, dysprosium nitrate, scandium nitrate, strontium nitrate, cesium nitrate, cerium (III) nitrate, thallium (I) nitrate, thallium (III) nitrate, iron (III) nitrate, copper (II) nitrate, sodium nitrate, lead (II) nitrate, nickel (II) nitrate, palladium (II) nitrate, barium nitrate, bismuth (III) nitrate, praseodymium (III) nitrate, holmium nitrate, magnesium nitrate, manganese (II) nitrate, europium (III) nitrate, lanthanum nitrate, lithium nitrate, rubidium nitrate, rhodium (III) nitrate, and the like. Examples of the double salt include urea nitrate and the like.

Examples of the nitric acid ester include isoamyl nitrate, isopropyl nitrate, isopentyl nitrate, and the like.

Preferable examples of the nitric compound include, for example, nitric acid, the metal salt of nitric acid, particularly such as zirconyl nitrate, indium nitrate, cerium nitrate, zinc nitrate, aluminum nitrate, ammonium nitrate, iron nitrate, copper nitrate, nickel nitrate, manganese nitrate or the like, and a mixture of nitric acid and the metal salt of nitric acid.

The nitric compound can be used neat in the form of a commercially available anhydride, hydrate, or a solution such as an aqueous solution or the like.

Although the amount of the nitric compound to be used is not particularly limited, it is generally in the range of from approximately 0.00001 to 2 moles per mol of the optically active vinyl-substituted cyclopropanecarboxylic acid compound of formula (1), or a catalytic amount, and preferably in the range of approximately 0.0001 to 0.3 mol, and more preferably, in the range of approximately 0.001 to 0.1 mol per mol of the optically active vinyl-substituted cyclopropanecarboxylic acid compound of formula (1).

Examples of the nitrogen oxide, which may be used in accordance with the present invention include, for example, dinitrogen monoxide, nitric monoxide, dinitroqen trioxide, nitrogen dioxide, dinitrogen tetroxide, and dinitrogen pentoxide. Preferred nitrogen oxide is nitrogen dioxide.

Liquid or gaseous nitrogen oxide can be used in the present process by suitably adjusting the reaction conditions and reactors.

Although the amount of the nitrogen oxide to be used is not particularly limited, it is generally a catalytic amount or in the range of approximately from 0.00001 to 2 moles per mol of the optically active vinyl-substituted cyclopropanecarboxylic acid compound (1), preferably in the range of approximately 0.0001 to 0.3 mol, and more preferably, in the range of approximately 0.001 to 0.2 mol per mol of the optically active vinyl-substituted cyclopropanecarboxylic acid compound (1).

The reaction of the vinyl-substituted cyclopropanecarboxylic acid compound (1) with a nitric compound or a nitrogen oxide may be conducted in an air atmosphere, however, it is preferably conducted in an atmosphere of an inert gas such as argon or nitrogen. Although the reaction may be conducted under a normal, pressurized or reduced pressure, it is preferably conducted under a normal pressure.

The reaction can be performed in the absence or presence of a solvent. Examples of the solvent which may be used include a halogenated hydrocarbon such as dichloromethane, chloroform, carbon tetrachloride, 1,2-dichloroethane, chlorobenzene or the like; an aliphatic hydrocarbon such as hexane, heptane, octane, nonane or the like; an aromatic hydrocarbon such as benzene, toluene, xylene or the like; an ether solvent such as diethyl ether, tetrahydrofuran or the like; and an aprotic or protic polar organic solvent such as dimethylformamide, dimethylsulfoxide, acetonitrile, acetic acid or the like.

The reaction temperature is not particularly limited, and the reaction is preferably conducted in the range of 0 to 250° C., and is more preferably 20 to 200° C., and even more preferably 40 to 180° C.

The vinyl-substituted cyclopropanecarboxylic acid compound thus produced in the present process can be readily separated from the reaction mixture by a conventional operation such as washing with water or acidic water, filtration, distillation, recrystallization, column chromatography, or the like.

In accordance with the present invention, the desired vinyl-substituted cyclopropanecarboxylic acid compound can be readily obtained in a good yield and good selectivity by subjecting the optically active vinyl-substituted cyclopropanecarboxylic acid compound of formula (1) to a reaction with a nitric compound or a nitrogen oxide.

EXAMPLES

The following examples further illustrate the present invention in more detail, however these examples do not limit the scope of the present invention.

Example 1

To a 15 ml tubular reaction vessel equipped with a condenser were charged 1.68 g of optically active 2,2-dimethyl-3-(2-methyl-1-propenyl) cyclopropanecarboxylic acid containing: 74.4% (+)-trans isomer[(1R, 3R)-isomer ]; 3.0% (−)-trans isomer[(1S, 3S)-isomer]; 23.1% (+)-cis isomer[(1R, 3S)-isomer]; and 0.5% (−)-cis isomer[(1S, 3R)-isomer], 0.032 g of nitric acid having a concentration of 93%, and 6 ml of xylene, and the resulting mixture was stirred under reflux of xylene for 8 hours. This reaction mixture was analyzed by HPLC using an optically active column and gas chromatography, which demonstrated that 2,2-dimethyl-3-(2-methyl-1-propenyl)-cyclopropanecarboxylic acid containing: 57.1% (+)-trans isomer; 29.9% (−)-trans isomer; 8.5% (+)-cis isomer; and 4.6% (−)-cis isomer was obtained in a yield of 99%.

Example 2

A reaction was performed in a similar manner as in Example 1, except that 0.27 g of zirconyl nitrate dihydrate was charged in place of 0.032 g of nitric acid. The reaction mixture was analyzed by HPLC using an optically active column and gas chromatography, which demonstrated that 2,2-dimethyl-3-(2-methyl-1-propenyl) cyclopropanecarboxylic acid containing: 48.9% (+)-trans isomer; 39.5% (−)-trans isomer; 6.2% (+)-cis isomer; and 5.4% (−)-cis isomer was obtained in a yield of 92%.

Example 3

A reaction was performed in a similar manner as in Example 1, except that 0.177 g of indium nitrate trihydrate was charged in place of 0.032 g of nitric acid. The reaction mixture was analyzed by HPLC using an optically active column and gas chromatography, which demonstrated that 2,2-dimethyl-3-(2-methyl-1-propenyl) cyclopropanecarboxylic acid containing: 50.4% (+)-trans isomer; 39.6% (−)-trans isomer; 5.4% (+)-cis isomer; and 4.5% (−)-cis isomer was obtained in a yield of 91%.

Example 4

A reaction was performed in a similar manner as in Example 1, except that 0.217 g of cerium nitrate hexahydrate was charged in place of 0.032 g of nitric acid. The reaction mixture was analyzed by HPLC using an optically active column and gas chromatography, which demonstrated that 2,2-dimethyl-3-(2-methyl-1-propenyl) cyclopropanecarboxylic acid containing: 50.8% (+)-trans isomer; 38.8% (−)-trans isomer; 5.7% (+)-cis isomer; and 4.7% (−)-cis isomer was obtained in a yield of 90%.

Example 5

To a 15 ml tubular reaction vessel equipped with a condenser were charged 1.96 g of optically active ethyl 2,2-dimethyl-3-(2-methyl-1-propenyl) cyclopropanecarboxylate containing: 92.5% (+)-trans isomer; 3.4% (−)-trans isomer; 3.1% (+)-cis isomer; and 1.0% (−)-cis isomer, 0.032 g of nitric acid having a concentration of 93%, and 6 ml of xylene, followed by stirring under reflux of xylene for 8 hours. This reaction mixture was analyzed by HPLC using an optically active column and gas chromatography, which demonstrated that ethyl 2,2-dimethyl-3-(2-methyl-1-propenyl) cyclopropanecarboxylate containing: 55.5% (+)-trans isomer; 32.5% (−)-trans isomer; 6.0% (+)-cis isomer; and 6.0% (−)-cis isomer was obtained in a yield of 99%.

Example 6

A reaction was performed in a similar manner as in Example 5, except that 0.134 g of zirconyl nitrate dihydrate was charged in place of 0.032 g of nitric acid. The reaction mixture was analyzed by HPLC using an optically active column and gas chromatography, which demonstrated that ethyl 2,2-dimethyl-3-(2-methyl-1-propenyl) cyclopropanecarboxylate containing: 43.0% (+)-trans isomer; 43.9% (−)-trans isomer; 6.5% (+)-cis isomer; and 6.6% (−)-cis isomer was obtained in a yield of 96%.

Example 7

A reaction was performed in a similar manner as in Example 5, except that 0.177 g of indium nitrate trihydrate was charged in place of 0.032 g of nitric acid. The reaction mixture was analyzed by HPLC using an optically active column and gas chromatography, which demonstrated that ethyl 2,2-dimethyl-3-(2-methyl-1-propenyl) cyclopropanecarboxylate containing: 49.2% (+)-trans isomer; 38.9% (−)-trans isomer; 5.9% (+)-cis isomer; and 5.9% (−)-cis isomer was obtained in a yield of 95%.

Example 8

To a 15 ml tubular reaction vessel equipped with a condenser were charged 1.96 g of optically active ethyl 2,2-dimethyl-3-(2-methyl-1-propenyl) cyclopropanecarboxylate containing: 92.5% (+)-trans isomer; 3.4% (−)-trans isomer; 3.1% (+)-cis isomer; and 1.0% (−)-cis isomer, and 0.134 g of zirconyl nitrate dihydrate, and the resulting mixture was stirred at 145° C. for 8 hours. This reaction mixture was analyzed on HPLC using an optically active column, and by gas chromatography, which demonstrated that the obtained ethyl 2,2-dimethyl-3-(2-methyl-1-propenyl) cyclopropanecarboxylate containing: 41.6% (+)-trans isomer; 44.7% (−)-trans isomer; 6.8% (+)-cis isomer; and 6.9% (−)-cis isomer was obtained in a yield of 93%.

Example 9

To a 50 ml tubular reaction vessel equipped with a condenser were charged 1.96 g of optically active ethyl 2,2-dimethyl-3-(2-methyl-1-propenyl) cyclopropanecarboxylate containing: 93.2% (+)-trans isomer; 2.8% (−)-trans isomer; 2.7% (+)-cis isomer; and 1.2% (−)-cis isomer, 0.028 g of nitric acid having a concentration of 65%, and 4 ml of xylene, and the resulting mixture was stirred under reflux of xylene for 4 hours. This reaction mixture was analyzed by HPLC using an optically active column and gas chromatography, which demonstrated that ethyl 2,2-dimethyl-3-(2-methyl-1-propenyl) cyclopropanecarboxylate containing: 47.3% (+)-trans isomer; 42.4% (−)-trans isomer; 5.1% (+)-cis isomer; and 5.2% (−)-cis isomer was obtained in a yield of 96%.

Example 10

To a 50 ml tubular reaction vessel equipped with a condenser were charged 0.98 g of optically active ethyl 2,2-dimethyl-3-(2-methyl-1-propenyl) cyclopropanecarboxylate containing: 93.2% (+)-trans isomer; 2.8% (−)-trans isomer; 2.7% (+)-cis isomer; and 1.2% (−)-cis isomer, 0.084 g of iron nitrate nonahydrate, and 2 ml of xylene, and the resulting mixture was stirred under reflux of xylene for 4 hours. This reaction mixture was analyzed by HPLC using an optically active column and gas chromatography, which demonstrated that ethyl 2,2-dimethyl-3-(2-methyl-1-propenyl)cyclopropanecarboxylate containing: 48.3% (+)-trans isomer; 41.6% (−)-trans isomer; 5.0% (+)-cis isomer; and 5.2% (−)-cis isomer was obtained in a yield of 88%.

Example 11

A reaction was performed in a similar manner as in Example 10, except that 0.061 g of zinc nitrate hexahydrate was charged in place of 0.082 g of iron nitrate. The reaction mixture was analyzed by HPLC using an optically active column and gas chromatography, which demonstrated that ethyl 2,2-dimethyl-3-(2-methyl-1-propenyl) cyclopropanecarboxylate containing: 59.7% (+)-trans isomer; 31.1% (−)-trans isomer; 4.6% (+)-cis isomer; and 4.6% (−)-cis isomer was obtained in a yield of 94%.

Example 12

A reaction was performed in a similar manner as in Example 10, except that 0.078 g of aluminum nitrate nonahydrate was charged in place of 0.082 g of iron nitrate. The reaction mixture was analyzed by HPLC using an optically active column and gas chromatography, which demonstrated that ethyl 2,2-dimethyl-3-(2-methyl-1-propenyl) cyclopropanecarboxylate containing: 44.0% (+)-trans isomer; 45.8% (−)-trans isomer; 5.0% (+)-cis isomer; and 5.2% (−)-cis isomer was obtained in a yield of 90%.

Example 13

To a 50 ml tubular reaction vessel equipped with a condenser were charged 0.98 g of optically active ethyl 2,2-dimethyl-3-(2-methyl-1-propenyl) cyclopropanecarboxylate containing: 93.2% (+)-trans isomer; 2.8% (−)-trans isomer; 2.7w (+)-cis isomer; and 1.2% (−)-cis isomer, 0.023 g of nitrogen dioxide, and 4 ml of xylene on an ice bath, and the resulting mixture was stirred under reflux of xylene for 4 hours. This reaction mixture was analyzed by HPLC using an optically active column and gas chromatography, which demonstrated that ethyl 2,2-dimethyl-3-(2-methyl-1-propenyl)cyclopropanecarboxylate containing: 48.3% (+)-trans isomer; 41.7% (−)-trans isomer; 5.0% (+)-cis isomer; and 5.1% (−)-cis isomer was obtained in a yield of 90%.

Example 14

To a 15 ml tubular reaction vessel equipped with a condenser were charged 1.68 g of optically active 2,2-dimethyl-3-(2-methyl-1-propenyl)cyclopropanecarboxylic acid containing: 74.4% (+)-trans isomer[(1R, 3R)-isomer]; 3.0% (−)-trans isomer[(1S, 3S)-isomer]; 23.1% (+)-cis isomer[(1R, 3S)-isomer]; and 0.5% (−)-cis isomer[(1S, 3R)-isomer], 0.019 g of nitric acid having a concentration of 65%, and 0.0038 g of $Al(NO_3)_3 \cdot 9H_2O$, and 6 ml of toluene, and the resulting mixture was stirred under reflux of toluene for 4 hours. This reaction mixture was analyzed by HPLC using an optically active column and gas chromatography, which demonstrated that 2,2-dimethyl-3-(2-methyl-1-propenyl)cyclopropanecarboxylic acid containing: 52.6% (+)-trans isomer; 38.1% (−)-trans isomer; 4.7% (+)-cis isomer; and 4.6% (−)-cis isomer was obtained in a yield of 98%.

What is claimed is:

1. A process for racemizing an optically active vinyl-substituted cyclopropanecarboxylic acid compound of formula (1):

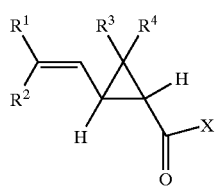

wherein $R^1$, $R^2$, $R^3$ and $R^4$ each independently represent
 a hydrogen atom, a halogen atom,
 an alkyl group having 1–4 carbon atoms, which may be substituted,
 an aryl group, which may be substituted, or an alkoxycarbonyl group, which may be substituted, or
 $R^1$ and $R^2$ are bonded to form an alkylene group, which may be substituted; and X represents a hydroxyl group, a halogen atom, an alkoxy group having 1–20 carbon atoms, which may be substituted, or an aryloxy group, which may be substituted, which process comprises reacting said optically active vinyl-substituted cyclopropanecarboxylic acid compound of formula (1) with a nitric compound selected from the group consisting of a nitrogen oxide, nitric acid, nitrate, and mixtures thereof.

2. The process according to claim 1, wherein the nitrate is a metal salt of nitric acid.

3. The process according to claim 2, wherein the metal salt of nitric acid is zirconyl nitrate, indium nitrate, cerium nitrate, zinc nitrate, aluminum nitrate, ammonium nitrate, iron nitrate, copper nitrate, nickel nitrate, or manganese nitrate.

4. The process according to claim 1, wherein the nitrogen oxide is nitrogen dioxide.

5. The process according to any one of claims 1, 2, 3, or 4, wherein $R^1$, $R_2$, $R_3$ and $R_4$ each represent a methyl group.

6. The process according to any one of claims 1, 2, 3, or 4, wherein $R^1$ and $R^2$ each represent a halogen atom, and $R^3$ and $R^4$ each represent a methyl group.

7. The process according to any one of claims 1, 2, 3, or 4, wherein the optically active vinyl-substituted cyclopropanecarboxylic acid compound of formula (1) is optically active 2,2-dimethyl-3-(1-propenyl)cyclopropanecarboxylic acid or optically active 2,2-dimethyl-3-(2-methyl-1-propenyl)cyclopropanecarboxylic acid.

8. The process according to any one of claims 1, 2, 3, or 4, wherein the vinyl-substituted cyclopropanecarboxylic acid compound of formula (1) is optically active 2,2-dimethyl-3-(1-propenyl)-cyclopropanecarboxylic acid chloride or optically active 2,2-dimethyl-3-2-methyl-1-propenyl)-cyclopropanecarboxylic acid chloride.

9. The process according to any one of claims 1, 2, 3, or 4, wherein the optically active vinyl-substituted cyclopropanecarboxylic acid compound of the formula (1) is optically active ethyl 2,2-dimethyl-3-Cl-propenyl)-cyclopropanecarboxylate or optically active ethyl 2,2-dimethyl-3-(2-methyl-1-propenyl) cyclopropanecarboxylate.

10. The method according to claim 1, wherein $R^1$, $R^2$, $R^3$ and $R^4$ each independently represent a hydrogen atom, a halogen atom, an alkyl group having 1–4 carbon atoms, which may be substituted with a group selected from a halogen atom, and an alkoxy group, an aryl group, which may be substituted with an alkyl group or a halogen atom, or an alkoxycarbonyl group, which may be substituted with a halogen atom, or $R^1$ and $R^2$ are bonded to form a haloalkylene group; and X represents a hydroxyl group, a halogen atom, an alkoxy group having 1–20 carbon atoms, which may be substituted with a halogen atom, an aryl group which may be substituted, a heterocyclic group, an oxo group, an alkenyl group an alkynyl group, a cyano group, a nitro group, or an aryloxy group, of which aromatic ring may be substituted with an alkyl, alkynyl, alkoxy, acetyl or formyl group, or a halogen atom.

11. The process according to claim 1, wherein the nitrate is a salt of nitric acid.

* * * * *